United States Patent
Uchiyama et al.

(10) Patent No.: US 7,410,614 B2
(45) Date of Patent: Aug. 12, 2008

(54) OPTICAL WAVEGUIDE TYPE IONTOPHORESIS SENSOR CHIP AND METHOD FOR PACKAGING SENSOR CHIP

(75) Inventors: Kenichi Uchiyama, Chigasaki (JP); Ikuo Uematsu, Yokohama (JP); Kayoko Oomiya, Yokohama (JP); Ichiro Tono, Yokohama (JP); Hideo Eto, Yokohama (JP); Isao Kishimoto, Yokohama (JP); Naotada Okada, Yokohama (JP); Masami Hirata, Yokkaichi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 865 days.

(21) Appl. No.: 10/899,264

(22) Filed: Jul. 26, 2004

(65) Prior Publication Data

US 2006/0063984 A1    Mar. 23, 2006

(51) Int. Cl.
*G01N 21/00* (2006.01)
*G02B 6/10* (2006.01)
(52) U.S. Cl. .................. 422/82.11; 385/12; 356/300
(58) Field of Classification Search ............ 422/82.11; 385/12; 356/300; 600/309, 310
See application file for complete search history.

(56) References Cited

U.S. PATENT DOCUMENTS

| | | | |
|---|---|---|---|
| 5,081,012 A * | 1/1992 | Flanagan et al. ............. 435/7.9 |
| 5,439,647 A * | 8/1995 | Saini ....................... 422/82.11 |
| 5,677,196 A * | 10/1997 | Herron et al. ............... 436/518 |
| 5,846,842 A * | 12/1998 | Herron et al. ............... 436/518 |
| D437,603 S * | 2/2001 | Liu ............................ D15/123 |
| 6,326,160 B1 | 12/2001 | Dunn et al. |
| 6,649,361 B1 * | 11/2003 | Iwasaki et al. ............... 435/7.4 |
| 6,687,522 B2 * | 2/2004 | Tamada ..................... 600/347 |
| 6,752,962 B2 * | 6/2004 | Carr et al. ................ 422/82.05 |
| 6,902,905 B2 * | 6/2005 | Burson et al. ................. 435/14 |
| 6,903,815 B2 * | 6/2005 | Uchiyama et al. ........... 356/305 |
| 7,022,515 B2 * | 4/2006 | Herron et al. ............. 435/287.1 |
| 7,052,652 B2 * | 5/2006 | Zanzucchi et al. ....... 422/82.05 |
| 7,054,514 B2 * | 5/2006 | Uchiyama et al. ............. 385/12 |
| 7,295,294 B2 * | 11/2007 | Shimazaki ................... 356/128 |
| 2002/0123152 A1 * | 9/2002 | Carr et al. ................... 436/164 |
| 2004/0062468 A1 * | 4/2004 | Lee ............................. 385/14 |
| 2005/0123451 A1 * | 6/2005 | Nomura ................... 422/82.11 |

* cited by examiner

*Primary Examiner*—Duane Smith
*Assistant Examiner*—Robert A Clemente
(74) *Attorney, Agent, or Firm*—Pillsbury Winthrop Shaw Pittman LLP

(57) ABSTRACT

An optical waveguide type iontophoresis sensor chip has a substrate having a first hinged plate and a second hinged plate, an optical waveguide plate connected to the first hinged plate and positioned over a first opening delineated in the first hinged plate, and a gel layer fixed on the second hinged plate and covering a second opening delineated in the second hinged plate and configured to contact with the optical waveguide plate through the first opening in case that the substrate is folded.

6 Claims, 3 Drawing Sheets

OPTICAL WAVEGUIDE TYPE IONTOPHORESIS SENSOR CHIP AND METHOD FOR PACKAGING SENSOR CHIP

BACKGROUND OF THE INVENTION

1. Field of the Invention

The present invention relates to an apparatus for measuring a specific molecule contained in body fluid and in particular to an optical waveguide type iontophoresis sensor chip and a method for packaging a sensor chip.

2. Description of the Related Art

A planar lightwave circuit sensor using optical waveguide phenomenon is widely spread as the sensor to measure the amount of the bio molecules existing in body fluid such as blood. The planar lightwave circuit sensor has a light source, a substrate receiving a light from the light source, and a pair of diffraction gratings disposed on the substrate. Between the pair of diffraction gratings, a single optical waveguide membrane is disposed on the substrate so as to transmit the incident light. Further, an analyzing membrane is disposed on the optical waveguide membrane. The analyzing membrane identifies the bio molecules and transforms the information about the amount of the identified bio molecules to a change of an optical intensity.

An existing method for analyzing the bio molecules contained in the blood by the planar lightwave circuit sensor is as follows. At first, the blood is collected from vein with a syringe. The collected blood is dropped on the analyzing membrane. The laser light is emitted and diffracted by a diffracting grating. The diffracted light penetrates the optical waveguide membrane. The evanescent wave is generated at the interface between the optical waveguide membrane and the analyzing membrane. The intensity of the evanescent wave changes by reaction between the dropped bio molecules contained in the blood and reagent contained in the analyzing membrane. By detecting the changes of the evanescent wave intensity, the bio molecules contained in the blood is analyzed as disclosed in Japanese Patent Application Hei9-61346.

On the other hand, a reverse iontophoresis method has also been studied recently. By the reverse iontophoresis method, the specific molecule is extracted from the living body through the skin with an electric current. Also, applying the reverse iontophoresis method to extract glucose from the living body without injury is attempted. By decomposing the extracted glucose with enzyme and detecting the amount of electron during the chemical reaction as the change of electric current, the enzyme electrode method is applied to develop an apparatus for measuring the glucose as disclosed in published Japanese Patent Application 2000-227 and published Japanese Patent Application 2002-191582.

However, the planar lightwave circuit sensor requires pricking part of the body with a needle and squeezing the body part. Though the enzyme electrode method does not require pricking the body, the result may be affected by the amount of enzyme contained in the extracted body fluid. Also, existing the enzyme electrode method using an electrode and immobilized glucose oxidase (GOD) can't continue the measurement after enzyme is exhausted.

SUMMARY OF THE INVENTION

An aspect of present invention inheres in an optical waveguide type iontophoresis sensor chip having a substrate having a first hinged plate and a second hinged plate, an optical waveguide plate connected to the first hinged plate and positioned over a first opening delineated in the first hinged plate, and a gel layer fixed on the second hinged plate and covering a second opening delineated in the second hinged plate and configured to contact with the optical waveguide plate through the first opening in case that the substrate is folded.

Another aspect of the present invention inheres in a method for packaging sensor chip containing covering two sides of a substrate having a first hinged plate and a second hinged plate with a packaging sheet, forming a first sealed cell by pasting the packaging sheet on a peripheral region of the first hinged plate, and forming a second sealed cell by pasting the packaging sheet on a peripheral region of the second hinged plate.

DETAILED DESCRIPTION OF THE INVENTION

Figure 1:
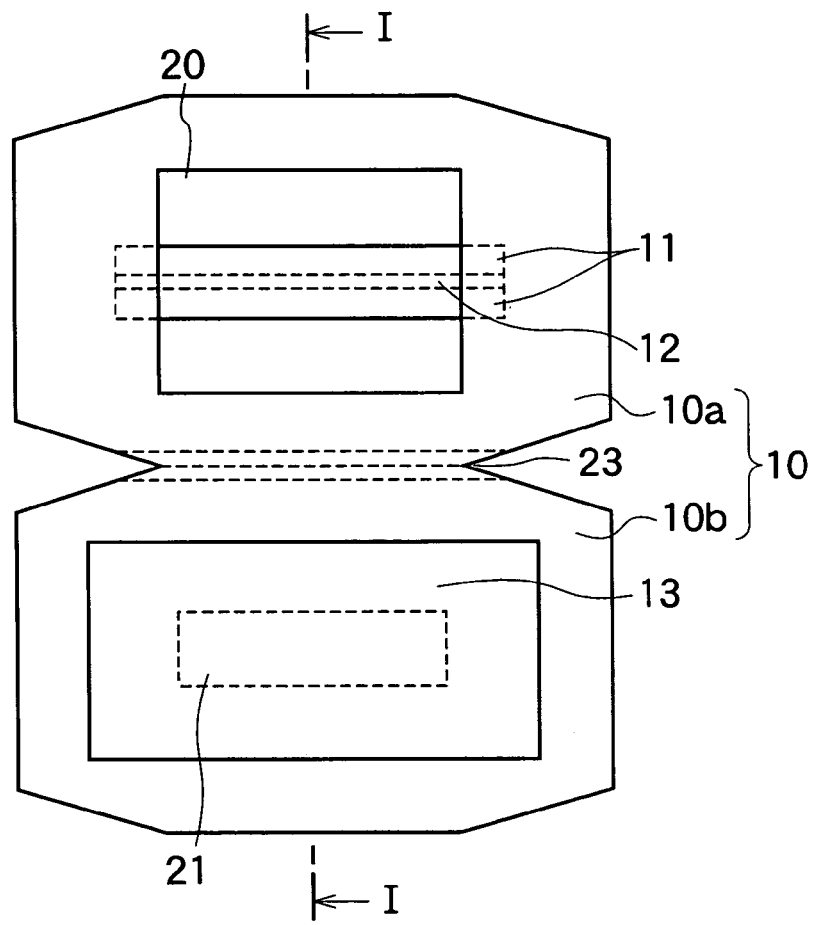
FIG. 1 is a plan view of an optical waveguide type iontophoresis sensor chip in accordance with an embodiment of the present invention.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

With reference now to FIG. 1, an optical waveguide type iontophoresis sensor chip in accordance with an embodiment of the present invention has a substrate 10. The substrate 10 has a sheet shape as a piece of paper and has a hinge groove 23 along centerline. The substrate 10 further has a first hinged plate 10a and a second hinged plate 10b on both sides of the hinge groove 23. The optical waveguide type iontophoresis sensor chip further has an optical waveguide plate 12 straddling a first opening 20 delineated in the first hinged plate 10a, and a gel layer 13 covering a second opening 21 delineated in the second hinged plate 10b. When the first hinged plate 10a is piled upon the second hinged plate 10b by folding along the hinge groove 23, the gel layer 13 contacts with the optical waveguide plate 12 through the first opening 20.

The substrate 10 is composed of a substance such as polyethylene terephthalate (PET), polystyrene, or polypropylene and has a sheet shape.

The optical waveguide plate 12 has a plate composed of transparent material such as indium tin oxide (ITO), tantalum oxide ($Ta_2O_5$), titanium oxide ($TiO_2$), or polystyrene. Enzyme, catalyst, and chromogenic reagent are immobilized on the plate so as to cause pigmentation with specific molecule in the body fluid. In case where the specific molecule is glucose, glucose oxidase (GOD) is used for the oxidized enzyme. And, peroxidase (POD) or platinum (Pt) is used for the catalyst. Also, N,N'-Bis(2-hydroxyl-3-sulfopropyl) tolidine disodium salt, or 3,3',5,5'-tetramethylbenzidine (TMBZ) is used for the chromogenic reagent, for example.

Oxidized enzyme reaction generates hydrogen peroxide. Further, reaction between the hydrogen peroxide and the POD generates oxygen radical (O*). The oxygen radical (O*) causes pigmentation of the chromogenic reagent. The reaction formulas (1)-(3) show reactions described above. It should be noted only product related to the pigmentation is shown in each of reaction formulas (1)-(3).

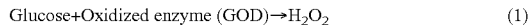
Glucose+Oxidized enzyme (GOD)→H₂O₂ (1)

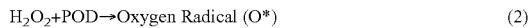
H₂O₂+POD→Oxygen Radical (O*) (2)

O*+Chromogenic reagent→Pigmentation (3)

Further, the optical waveguide plate 12 has diffraction gratings in incident portion and irradiation portion at the both ends of the optical waveguide plate 12 so as to couple tight beam and decouple the light beam. It is desirable that the optical waveguide plate 12 is protected from impurities such as fingerprints during the handling, since surface of the optical waveguide plate 12 irradiates light. Therefore, it is desirable that a pair of protection plates 11 is disposed on the surface of the optical waveguide plate 12 opposing to the contact surface on the substrate 10. The pair of the protection plates 11 has an interval of substantially 1 mm for optical transmission.

The gel layer 13 is a hydrate gel containing sodium chloride, for example. The gel layer 13 is configured to contact with a living body and serves as the anode when an electric field is applied to the living body. The gel layer 13 absorbs the body fluid extracted from the living body when the electric field is applied to the living body.

Figure 2:
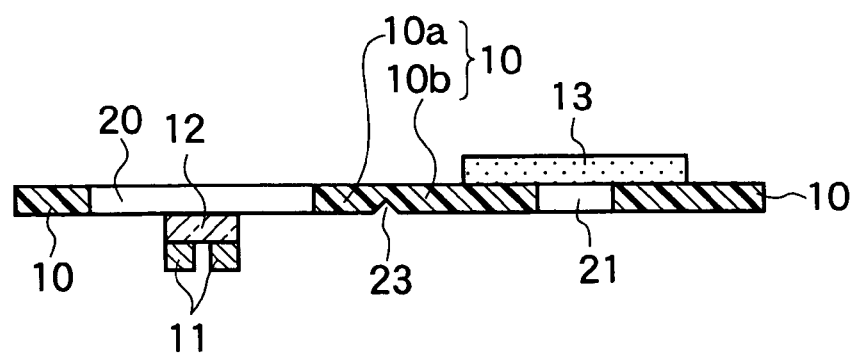
FIG. 2 is a cross section of the optical waveguide type iontophoresis sensor chip in a direction of a line I-I shown in FIG. 1 in accordance with the embodiment of the present invention.

Also, it is desirable that the hinge groove 23 is formed in boundary region between the first hinged plate 10a and the second hinged plate 10b on the substrate 10 so as to fold the substrate 10 easily. As shown in FIG. 2, the first opening 20 and the second opening 21 are delineated on both sides of the hinge groove 23. Beneath the first opening 20, the optical waveguide plate 12 connected to the substrate 10 is positioned. The gel layer 13 connected to the substrate 10 is positioned over the second opening 21. Further, the pair of the protection plates 11 is disposed on the surface of the optical waveguide plate 12 opposing to the surface facing the first opening 20.

Figure 3:
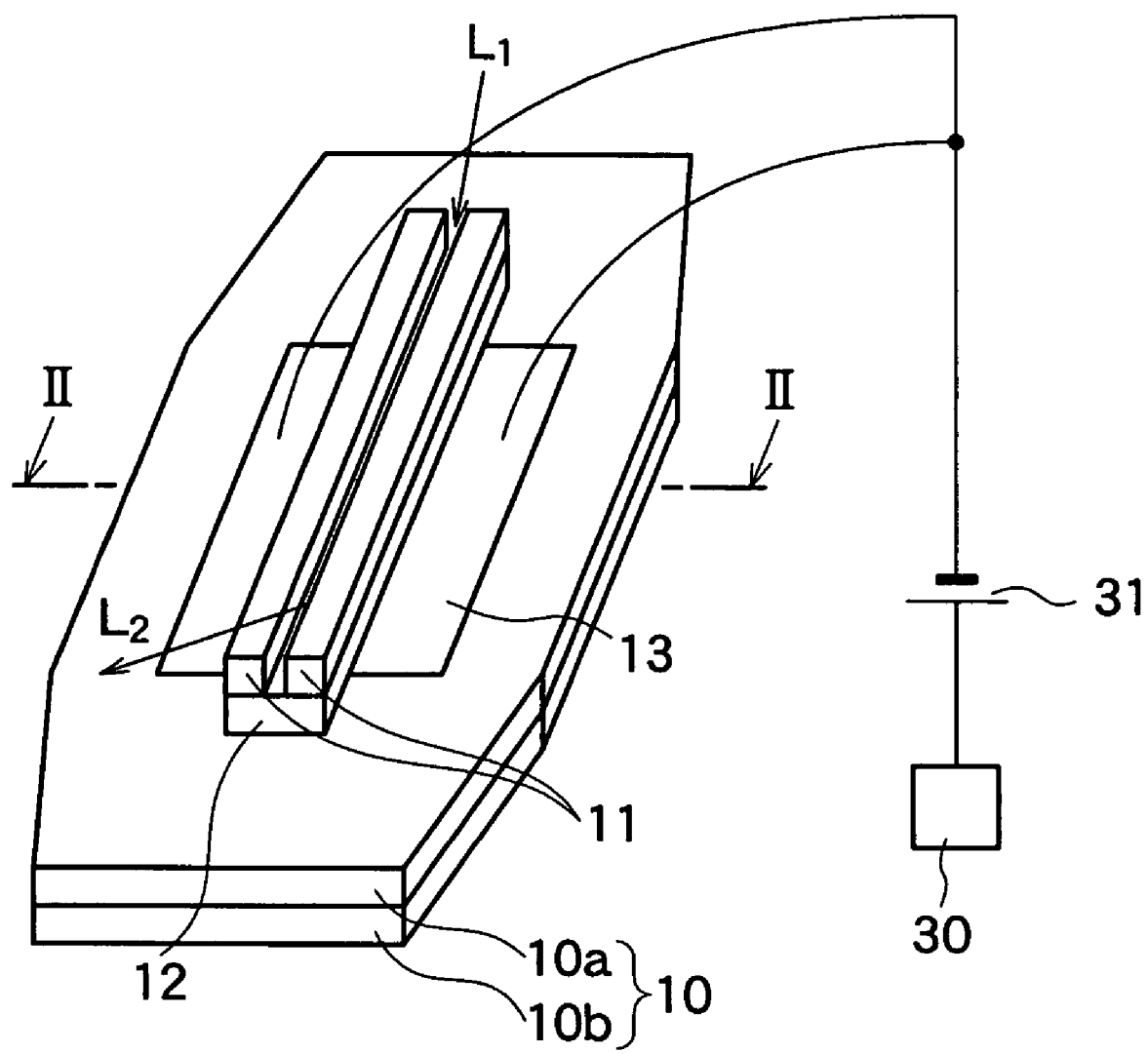
FIG. 3 is an exploded perspective view of the optical waveguide type iontophoresis sensor chip in accordance with the embodiment of the present invention.
Figure 4:
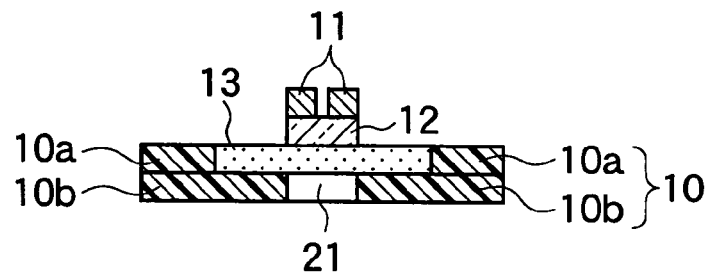
FIG. 4 is a cross section of the optical waveguide type iontophoresis sensor chip in a direction of a line II-II shown in FIG. 3 in accordance with the embodiment of the present invention.

With reference next to FIG. 3, the substrate 10 is folded when the optical waveguide type iontophoresis sensor chip is used. The anode of a power supply 31 is contacted with the gel layer 13 exhibited by the first opening 20 on the both sides of the optical waveguide plate 12. The cathode of the power supply 31 is contacted to a cathode plate 30. As shown in FIG. 4, the second opening 21 is positioned beneath the surface of the gel layer 13 opposing to the surface facing the optical waveguide plate 12. When the optical waveguide type iontophoresis sensor chip is placed on the living body with the optical waveguide plate 12 up, a first portion of skin may contact with the gel layer 13. Therefore, it is possible to add the electric field between the gel layer 13 and the cathode plate 30 by connecting the cathode plate 30 with a second portion of the skin. Subsequently, the gel layer 13 serving as the anode may extract the body fluid from the skin by reverse iontophoresis. Consequently, the reaction described as the formula (1)-(3) causes the pigmentation on the surface of the optical waveguide plate 12.

As shown in depicted arrows of FIG. 3, the incident laser beam L1 penetrates into the optical waveguide plate 12. And, the irradiated laser beam L2 from the optical waveguide plate 12 may be measured. In this case, the evanescent wave is generated at the interface between the optical waveguide plate 12 and the gel layer 13. The evanescent wave is absorbed by the pigmentation. Therefore, it is possible to estimate the concentration of the specific molecules contained in the body fluid from the difference between the intensities of the incident laser beam L1 and the irradiated laser beam L2.

Figure 5:
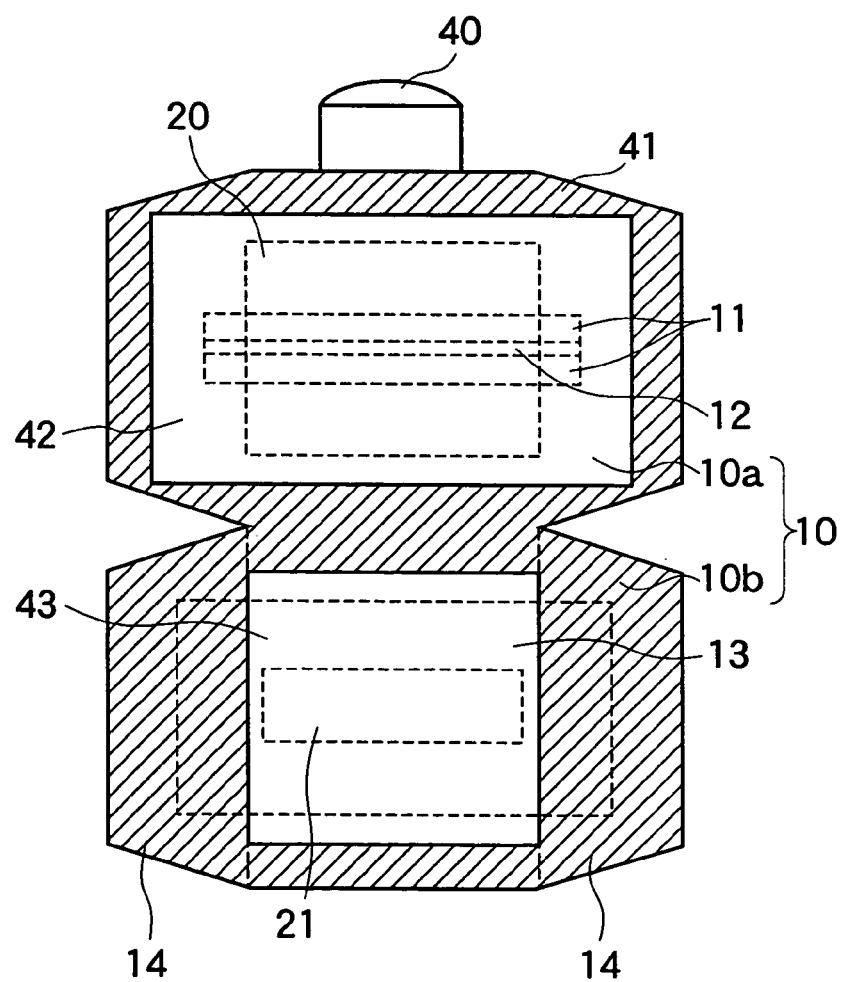
FIG. 5 is a plan view of the packaged optical waveguide type iontophoresis sensor chip in accordance with the embodiment of the present invention.

With reference next to FIG. 5, the method for manufacturing a packaged optical waveguide type iontophoresis sensor chip is described as follows.

(a) Two sides of the substrate 10 are covered with packaging sheet such as laminated sheet of polyethylene aluminum.

(b) A first sealed cell 42 is formed by pasting the packaging sheet on a peripheral region of the first hinged plate 10a under pressure.

(c) A second sealed cell 43 is formed by pasting the packaging sheet on a peripheral region of the second hinged plate 10b under pressure.

(d) To fix the both ends of the gel layer 13 on the substrate 10, the packaging sheet and the both ends of the gel layer 13 are bonded under pressure to form a gel holding portion 14.

Finally, a tab portion 41 is formed by the packaging sheet and is pasted on the substrate 10. The tab portion 41 is indicated by oblique lines in FIG. 5. Consequently, the first sealed cell 42 seals in the optical waveguide plate 12. By employing the protection plates 11 containing desiccating agent such as silica gel, it becomes possible to keep the interior of the first sealed cell 42 dry. On the other hand, the second sealed cell 43 seals in the gel layer 13. Thus it becomes possible to keep the moisture content of the gel layer 13.

The reason why the gel holding portion 14 is pasted on the substrate 10 is only gel holding portion 14 is left when the packaging sheet is opened and the tab portion 41 is torn up and removed. Therefore, the gel portion 14 makes it possible to fix the gel layer 13 to the substrate 10 after the tab portion 41 is removed. Accordingly, there is no need to glue the gel layer 13 into the substrate 10. In this case, it is desirable to establish a pull 40 in the packing sheet. The pull 40 is a convex region of the packing sheet covering the two sides of the substrate 10. The pull 40 separates package sheet covering two sides of substrate 10. By pulling the pull 40, the laminated sheet on the gel layer 13 side may be torn up in the direction of pulling.

As described above, the optical waveguide type iontophoresis sensor chip in accordance with an embodiment of the present invention makes it possible to apply the electric field to the living body and accordingly extract the body fluid from the living body with reverse iontophoresis method. Therefore, there is no need to prick part of the body with a needle and squeeze the body part. Also, the optical waveguide type iontophoresis sensor chip makes it possible to measure the concentration of the specific molecule in the body fluid.

Further, it is possible to manufacture the optical waveguide type iontophoresis sensor chip by cheap materials. Therefore, it becomes possible to provide the optical waveguide type iontophoresis sensor chip with low price and decrease user's cost.

OTHER EMBODIMENTS

Although the invention has been described above by reference to the embodiment of the present invention, the present invention is not limited to the embodiment so described.

Modifications and variations of the embodiment so described will occur to those skilled in the art, in the light of the above teachings.

Though a structure to stick the first and second hinged plates 10a, 10b firmly is not described in the embodiment, a hook to inlay a portion of the first hinged plate 10a into a portion of the second hinged plate 10b may be established in the substrate 10, for example. Such hook is useful to fix the first hinged plate 10a on the second hinged plate 10b firmly in case where the substrate 10 is folded. Also, various types and a number of hooks can be applied to the substrate 10.

Therefore, the scope of the invention is defined with reference to the following claims.

What is claimed is:

1. An optical waveguide type iontophoresis sensor chip comprising:
   a substrate having a first hinged plate and a second hinged plate;
   an optical waveguide plate connected to the first hinged plate and positioned over a first opening delineated in the first hinged plate; and
   a gel layer fixed on the second hinged plate and covering a second opening delineated in the second hinged plate and configured to contact with the optical waveguide plate through the first opening in case that the substrate is folded.

2. The optical waveguide type iontophoresis sensor chip of claim 1, further comprising a pair of protection plates having an interval for light transmission and disposed on an opposite surface of the optical waveguide plate to a contact surface on the substrate.

3. The optical waveguide type iontophoresis sensor chip of claim 2, wherein the pair of the protection plate contains a desiccating agent.

4. The optical waveguide type iontophoresis sensor chip of claim 1, further comprising a hinge groove along a boundary between the first hinged plate and the second hinged plate.

5. The optical waveguide type iontophoresis sensor chip of claim 1, further comprising;
   a first sealed cell that is formed by pasting a packaging sheet on a peripheral region of the first hinged plate and seals in the optical waveguide plate;
   a gel holding portion formed by the packaging sheet and fixing the both ends of the gel layer on the substrate; and
   a second sealed cell that is formed by pasting the packaging sheet on a peripheral region of the second hinged plate and seals in the gel layer.

6. The optical waveguide type iontophoresis sensor chip of claim 5, wherein the gel holding portion is left on the substrate in case that the packaging sheet is opened.

* * * * *